(12) United States Patent
Moriyama

(10) Patent No.: US 7,326,175 B2
(45) Date of Patent: Feb. 5, 2008

(54) ENDOSCOPE HOOD

(75) Inventor: Hiroki Moriyama, Akishima (JP)

(73) Assignee: Olympus Corporation (JP)

( * ) Notice: Subject to any disclaimer, the term of this patent is extended or adjusted under 35 U.S.C. 154(b) by 411 days.

(21) Appl. No.: 10/687,181

(22) Filed: Oct. 16, 2003

(65) Prior Publication Data

US 2004/0082832 A1    Apr. 29, 2004

Related U.S. Application Data

(63) Continuation of application No. PCT/JP03/04431, filed on Apr. 8, 2003.

(30) Foreign Application Priority Data

Apr. 8, 2002    (JP)    ............................ 2002-105349

(51) Int. Cl.
*A61B 1/00*    (2006.01)
(52) U.S. Cl. ........................ 600/127; 600/128; 600/129
(58) Field of Classification Search ........ 600/121–125, 600/127, 129
See application file for complete search history.

(56) References Cited

U.S. PATENT DOCUMENTS

| | | | | |
|---|---|---|---|---|
| 5,667,475 A | * | 9/1997 | Laser et al. ................. | 600/127 |
| 5,897,487 A | * | 4/1999 | Ouchi ......................... | 600/127 |
| 5,976,073 A | * | 11/1999 | Ouchi ......................... | 600/129 |
| 6,306,081 B1 | * | 10/2001 | Ishikawa et al. ............ | 600/127 |
| 6,855,108 B2 | * | 2/2005 | Ishibiki et al. .............. | 600/127 |
| 2002/0032367 A1 | | 3/2002 | Akiba ......................... | 600/127 |
| 2003/0088154 A1 | * | 5/2003 | Ishibiki et al. .............. | 600/127 |

FOREIGN PATENT DOCUMENTS

| | | |
|---|---|---|
| JP | 11-76155 | 3/1999 |
| JP | 11-313795 | 11/1999 |
| JP | 2001-224550 | 8/2001 |
| JP | 2002-51970 | 2/2002 |
| JP | 2002-95623 | 4/2002 |

OTHER PUBLICATIONS

Office Action from Japanese Patent Office issued Jan. 18, 2005 in connection with corresponding Japanese application No. 20002-105349.
English translation of Japanese Office Action issued Jan. 18, 2005.
English translation of International Search Report dated Apr. 24, 2003 in relation to PCT/JP03/04431.

* cited by examiner

*Primary Examiner*—Linda C. M. Dvorak
*Assistant Examiner*—Matthew J. Kasztejna
(74) *Attorney, Agent, or Firm*—Ostrolenk, Faber, Gerb & Soffen, LLP

(57) ABSTRACT

At the time of irradiation of illumination light rays of an endoscope, a shadow is eliminated by leading illumination light rays passing through a second concave portion of a protruding portion of a hood main body to a shadow part of the protruding portion of the hood main body formed in an observation visual field range of the endoscope.

14 Claims, 4 Drawing Sheets

ENDOSCOPE HOOD

CROSS-REFERENCE TO RELATED APPLICATIONS

This is a Continuation Application of PCT Application No. PCT/JP03/04431, filed Apr. 8, 2003, which was not published under PCT Article 21(2) in English.

This application is based upon and claims the benefit of priority from the prior Japanese Patent Application No. 2002-105349, filed Apr. 8, 2002, the entire contents of which are incorporated herein by reference.

BACKGROUND OF THE INVENTION

1. Field of the Invention

The present invention relates to an endoscopic hood having a cylindrical hood main body attached to an end portion of an insertion portion of an endoscope.

2. Description of the Related Art

Generally, an endoscopic hood may be used in a state that it is attached to an end portion of an insertion portion of an endoscope in some cases. This endoscopic hood is attached in a state that it is detachably disposed to an end portion of an insertion portion or that it is integrally fixed to the same.

FIG. 7A shows a state that a conventional endoscopic hood b is attached to an end portion of an insertion portion a of an endoscope. Here, to an end surface a1 of the insertion portion a of the endoscope are provided an object lens c of an observation optical system and an illumination lens d of an illumination optical system, respectively. Further, an observation visual field is illuminated with illumination light rays emitted from the illumination lens d. At this moment, an observation image in the observation visual field in an illumination range illuminated with the illumination light enters the object lens c. As a result, the observation image of the endoscope is displayed on a screen of, e.g., a monitor.

Furthermore, a substantially cylindrical hood main body ba is provided to the endoscopic hood b. A fixed portion b2 fixed to the end portion of the insertion portion a of the endoscope is provided on a base end side of this hood main body b1.

Moreover, a protruding portion b3 which protrudes in an observation visual field direction of the endoscope is extended to the end portion of this fixed portion b2. Additionally, when an end surface a1 of the insertion portion a of the endoscope approximates an intraluminal wall surface, the protruding portion b3 is designed to come into contact with the intraluminal wall surface before the object lens c of the observation optical system is brought into contact with the intraluminal wall surface. As a result, the endoscopic hood b prevents the object lens c of the observation optical system exposed on the end surface a1 of the insertion portion a from directly coming into contact with the intraluminal wall surface.

In observation using the endoscope, incident light rays entering the object lens c are restricted within a range of an extension line (indicated by a solid line in FIG. 7A) running between an end edge of the protruding portion b3 of the endoscopic hood b and the object lens c. Further, the distance between a living tissue as an observation target and the object lens c and a display range (observation range) of the living tissue as an observation target inserted into the observation visual field of the object lens c varies in proportion. Therefore, when the distance between the living tissue as the observation target and the object lens c is large, the range of the observation target inserted into the observation visual field of the object lens c becomes large. For example, when performing an operation to search for a target diseased part, this operation is carried out in a state that the distance between the living tissue as the observation target and the object lens c is large and the display range of the living tissue is wide.

Furthermore, after the target diseased part is found, the end portion of the insertion portion a of the endoscope is caused to approximate the target diseased part. As a result, the target diseased part is magnified as much as possible and displayed in detail. At this moment, by bringing the end of the protruding portion b3 of the endoscopic hood b into contact with the living tissue, the distance between the living tissue as the observation target and the object lens c is maintained as a fixed distance.

Moreover, Jpn. Pat. Appln. KOKAI publication No. 2001-224550 discloses a structure that an inner wall part of the endoscopic hood is formed into a square-built shape along an outer edge of the observation visual field of the rectangular observation optical system. This prevents the rectangular observation visual field of the observation optical system from being cut off by the inner wall part of the endoscopic hood.

Meanwhile, the endoscopic hood b may be used in a state that the end portion of the protruding portion b3 is in contact with the living tissue in some cases. Therefore, the endoscopic hood b3 is generally formed of a soft material such as rubber. This soft material such as rubber cannot transmit the light therethrough. Thus, in observation using the endoscope, the irradiation range of the illumination light emitted from the illumination lens d is restricted by an end position of the protruding portion b3 of the endoscopic hood b.

Additionally, even when the endoscopic hood b is used with the end portion of the protruding portion b3 being in contact with the living tissue, the object lens c of the observation optical system must be focused on the living tissue. Therefore, a fixed length is required as a protrusion length of the protruding portion b3 of the endoscopic hood b.

Further, the object lens c and the illumination lens d on the end surface a1 of the insertion portion a of the endoscope are arranged at positions displaced in a direction orthogonal to an axial direction of the insertion portion a of the endoscope. Therefore, as shown in FIG. 7A, a deviation occurs in an irradiation range (irradiation angle $\alpha$) of the illumination light emitted from the illumination lens d indicated by the chain double-dashed line in FIG. 7A and a visual field range (observation angle $\beta$) of an observation image entering the object lens c indicated by a solid line in FIG. 7A.

Here, when the endoscopic hood b that the protrusion length of the protruding portion b3 of the endoscopic hood b is set at a limit position which is not included in the visual field range of the object lens c is attached at the end portion of the insertion portion a of the endoscope, the protruding portion b3 of the endoscopic hood b is not inserted into the visual field range of the object lens c. In this case, however, a part of the illumination light with which the visual field range of the object lens c is irradiated is cut off by the protruding portion b3 of the endoscopic hood b. Therefore, as shown in FIG. 7B, there is a problem of occurrence of so-called vignetting of the illumination light that a shadow f of the protruding portion b3 of the endoscopic hood b is inserted into an observation image of the endoscope displayed in a screen e of a monitor. In this case, there is generated a problem that the display range of the observation image of the endoscope displayed in the screen e of the monitor is narrower than the visual field range of the observation image entering the object lens c.

In view of the above-described problems, it is an object of the present invention to provide an endoscopic hood with an excellent observation performance, which can reduce shadow in an observation screen of an endoscope caused due to vignetting of the illumination light without degrading the function of the hood main body.

BRIEF SUMMARY OF THE INVENTION

An endoscopic hood according to the present invention comprises:

a cylindrical hood main body which has an attachment portion attached in a state that it is fitted onto an end portion outer peripheral surface of an insertion portion of an endoscope, and a protruding portion which protrudes from an end surface of the insertion portion of the endoscope in an axial direction of the insertion portion; and an illumination light leading portion which is provided to the protruding portion and transmits therethrough an illumination light ray with which a part of an observation visual field range of an object lens of the endoscope is illuminated, the illumination light leading portion being arranged at such a position that a distance from an illumination lens which emits the illumination light of the endoscope is shorter than a distance from the object lens of the endoscope.

Furthermore, in the present invention, when emitting the illumination light of the endoscope, the illumination light passing through the illumination light leading portion of the protruding portion is led into a shadow part of the protruding portion formed in the observation visual field range of the endoscope in order to eliminate the shadow of the protruding portion.

According to the present invention, it is possible to provide an endoscopic hood with an excellent observation performance, which can reduce the shadow in an observation screen of an endoscope caused due to vignetting of the illumination light without degrading the function of the hood main body.

Moreover, according to the present invention, the illumination light leading portion preferably has a concave portion formed by notching the end portion of the protruding portion.

Additionally, in the present invention, when emitting the illumination light of the endoscope, the illumination light passing through the concave portion of the end portion of the protruding portion is led to a shadow part of the protruding portion formed in the observation visual field range of the endoscope, thereby eliminating the shadow of the protruding portion.

According to the present invention, the illumination light leading portion preferably has at least one hole formed on a wall surface of the protruding portion.

Further, in the present invention, when emitting the illumination light of the endoscope, the illumination light passing through the hole on the wall surface of the protruding portion is led to a shadow part of the protruding portion formed in the observation visual field range of the endoscope, thereby eliminating the shadow of the protruding portion.

According to the present invention, a peripheral wall of the hole of the protruding portion is preferably set to substantially the same angle as an outgoing radiation angle of the illumination light outgoing from the illumination lens.

Furthermore, in the present invention, when emitting the illumination light of the endoscope, the illumination light passing through the hole on the wall surface of the protruding portion is led to a shadow part of the protruding portion formed in the observation visual field range of the endoscope, thereby eliminating the shadow of the protruding portion.

DETAILED DESCRIPTION OF THE INVENTION

Figure 1:
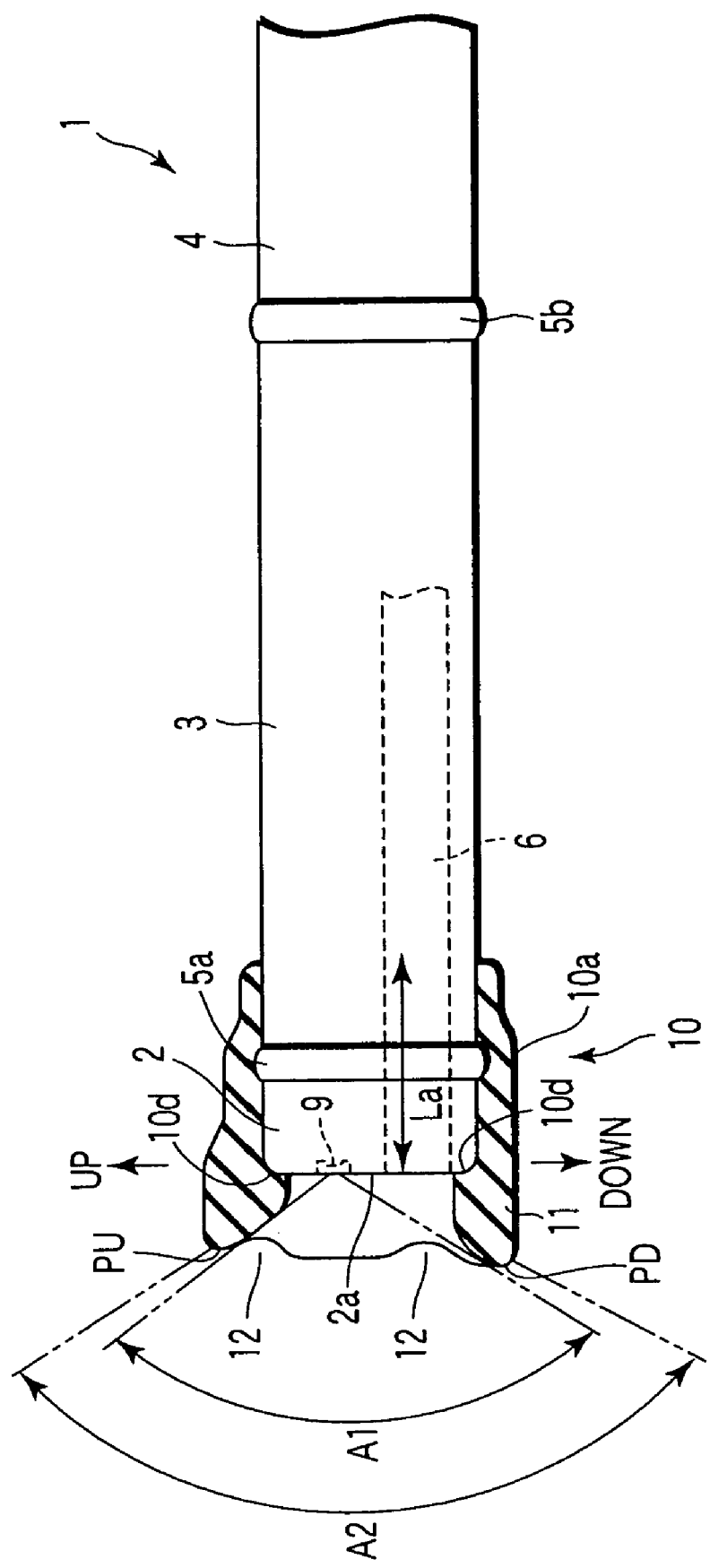
FIG. 1 is a vertical cross-sectional view showing an attachment state of an endoscopic hood in a first embodiment according to the present invention.

A first embodiment according to the present invention will now be described hereinafter with reference to FIGS. 1 to 4. FIG. 1 shows a schematic structure of an end part of an insertion portion 1 of an endoscope inserted into a lumen. An elongated soft portion 4 having the flexibility is provided to the insertion portion 1. A bending portion 3 which can bend is provided on an end side of the soft portion 4.

A hard end portion 2 is arranged at an endmost part of the insertion portion 1. On the end portion 2 are provided an observation optical system, an illumination optical system and others as will be described later.

The end portion 2 and the bending portion 3 are connected to each other through a first connection portion 5a, and the bending portion 3 and the soft portion 4 are connected to each other through a second connection portion 5b. A non-illustrated front side operation portion is coupled to a base end portion of the soft portion 4. To the operation portion is provided a non-illustrated bending operation input portion such as a bending operation knob or a joystick. Moreover, the bending portion 3 is remotely bent and operated by manipulation of the bending operation input portion.

Figure 2:
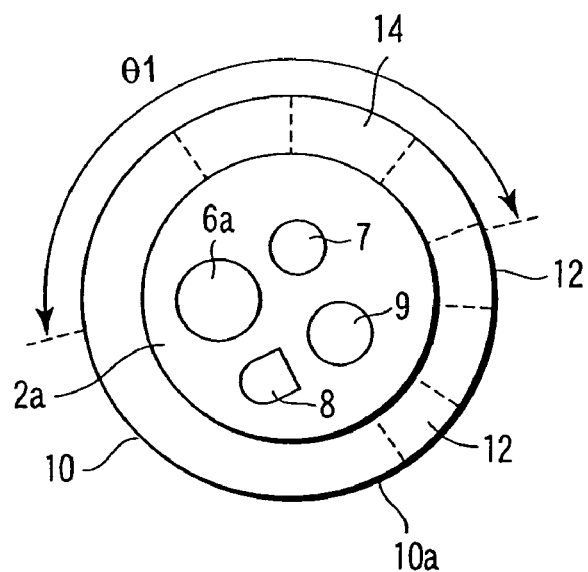
FIG. 2 is a front view showing an end surface of an endoscope to which the endoscopic hood according to the first embodiment is attached.

Additionally, as shown in FIG. 2, on an end surface 2a of the end portion 2 are provided one end opening portion 6a, one illumination lens 7, one object lens 9 and one air supply/water supply nozzle 8, respectively. The end opening portion 6a is coupled to a treatment tool insertion channel 6 extended inside the insertion portion 1 in an axial direction. The illumination lens 7 constitutes a part of the illumination optical system. The object lens 9 constitutes a part of the observation optical system. An injection hole of the air supply/water supply nozzle 8 is arranged facing the object lens 9. A non-illustrated air supply/water supply operation button is arranged on the operation portion on the front side. Further, a cleansing liquid or a gas (air) is injected from the air supply/water supply nozzle 8 toward the object lens 9 by an air supply operation or a water supply operation of the air supply/water supply operation button.

Furthermore, a non-illustrated treatment tool insertion opening and a non-illustrated suction operation button are provided on the operation portion on the front side. A base end portion of the treatment tool insertion channel 6 communicates with the treatment tool insertion opening. Moreover, a treatment tool inserted from the treatment tool insertion opening passes through the treatment tool insertion channel 6, and is extended from an end opening portion 6a to the outside.

Additionally, a non-illustrated suction duct is coupled to a middle portion of the treatment tool insertion channel 6. Further, a liquid in a lumen is sucked by performing a suction operation from the end opening portion 6a into the treatment tool insertion channel 6 by manipulating the non-illustrated suction operation button.

Further, an endoscopic hood 10 is detachably attached to the end portion 2. In the endoscopic hood 10, a substantially cylindrical hood main body 10a is formed of a soft member, e.g., vulcanized rubber such as silicon rubber or fluorine rubber, or thermoplastic elastomer such as urethane-based elastomer, acrylic elastomer or olefin-based elastomer.

Figure 3:
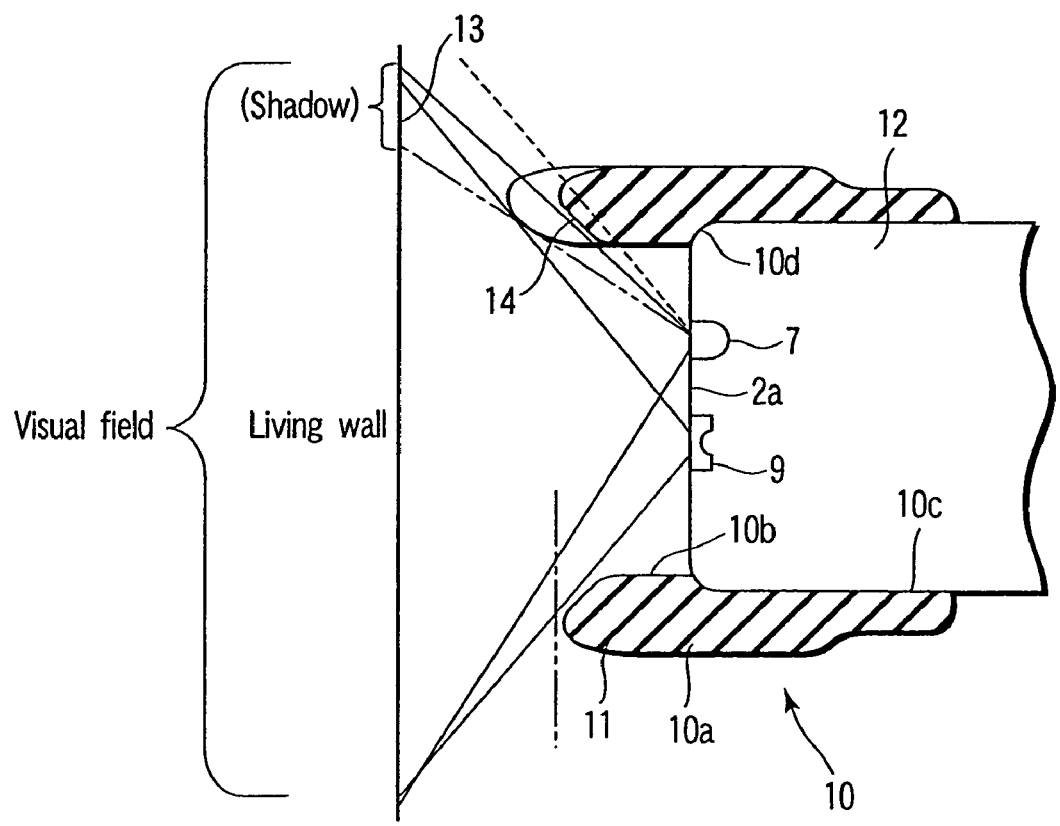
FIG. 3 is a vertical cross-sectional view showing a primary part of an illuminating light leading portion of the endoscopic hood according to the first embodiment.

As shown in FIG. 3, in the cylinder of the hood main body 10a, a small-diameter portion 10b is provided on the end portion side and a large-diameter endoscope fixing portion 10c is provided on a rear portion side away from this small-diameter portion 10b, respectively. Here, an inside diametric dimension of the endoscope fixing portion 10c is formed equal to or slightly smaller than an outside diametric dimension of the end portion 2 of the endoscope. An impingement end portion 10d of the end portion 2 of the endoscope is formed at a step portion between the small-diameter portion 10b of the hood main body 11a and the endoscope fixing portion 10c. Furthermore, when attaching the endoscopic hood 10 to the end portion 2 of the endoscope, the end portion 2 of the endoscope is press-fitted into the endoscope fixing portion 10c of the hood main body 10a from the rear end side of the endoscopic hood 10. At this moment, the end portion 2 of the endoscope is press-fitted to a front end portion of the endoscope fixing portion 10c of the hood main body 10a by elastic deformation of the endoscope fixing portion 10c. Moreover, with the end portion 2 of the endoscope being pressed against the impingement end portion 10d, the endoscopic hood 10 is detachably fixed to the end portion 2 of the endoscope. It is to be noted that a length of the endoscope fixing portion 10c is set shorter than a length La of a hard portion of the end portion 2 of the endoscope as shown in FIG. 1.

Additionally, to the hood main body 10a is provided a protruding portion 11 which protrudes from the end portion 2 of the endoscope in a direction of the front of a visual field of the observation optical system. In this embodiment, a protrusion length of the protruding portion 11 is set to, e.g., approximately 3 mm to 5 mm. Although it varies depending on each model, since it is often the case that a point of the object lens 9 of the endoscope on a near point side of an observation depth is set to approximately 3 mm to 5 mm, the protrusion length of the protruding portion 11 is set in accordance with this value. Further, when the end surface 2a of the insertion portion 1 of the endoscope approximates an intraluminal wall surface, the protruding portion 11 is designed to come into contact with the intraluminal wall surface before the object lens 9 of the observation optical system is brought into contact with the intraluminal wall surface. As a result, the endoscopic hood 10 prevents the object lens 9 of the observation optical system exposed on the end surface 2a of the insertion portion 1 from directly coming into contact with the intraluminal wall surface, thereby avoiding loss of the visual field of the endoscope.

Furthermore, at the end portion of the protruding portion 11 of the hood main body 10a according to this embodiment, two first concave portions 12 and one second concave portion (illumination light leading portion) 14 are provided at a part in a circumferential direction as shown in FIG. 2. The first concave portion 12 avoids so-called visual field vignetting that the visual field of the endoscope is cut off by the end portion of the protruding portion 11. The second concave portion 14 is a shadow elimination concave portion which prevents so-called vignetting of the illumination light that a shadow 13 of the protruding portion 11 of the endoscope hood 10 is inserted into an observation image of the endoscope.

Figure 4:
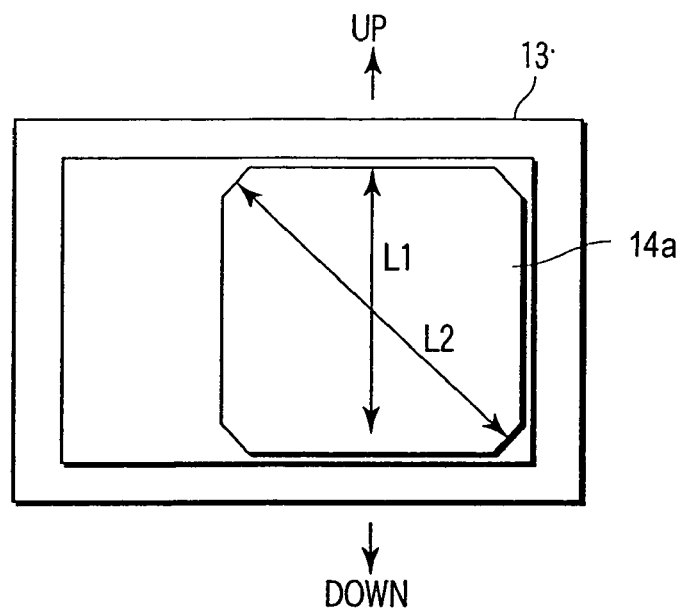
FIG. 4 is a front view showing an observation image of an observation optical system of an endoscope displayed on a monitor of an endoscopic apparatus according to the first embodiment.

Here, the first concave portion 12 of the protruding portion 11 of the hood main body 10a is set as follows. That is, as shown in FIG. 4, an observation image 14a of the endoscope displayed in the monitor 13 of the endoscopic apparatus is formed into a substantially rectangular shape. This observation image 14a has a length L2 in a diagonal direction larger than a length L1 in an opposite side direction. Here, a visual field angle of the object lens 9 of the endoscope has the following relationship. As shown in FIG. 1, assuming that a visual field angle in a direction corresponding to the length L1 in the opposite side direction of the observation image 14a is A1 and a visual field angle corresponding to the length L2 in the diagonal direction of the observation image 14a is A2, A2 is larger than A1. Further, when the protrusion length of the protruding portion 11 of the endoscopic hood 10 is formed to be fixed over the entire circumferential direction in accordance with the visual field angle A1, there occurs so-called visual field vignetting which is a phenomenon where the visual field of the object lens 9 of the endoscope is cut off by the end portion of the protruding portion 11 of the endoscopic hood 10 around the visual field angle A2 corresponding to the length L2 in the diagonal direction of the observation image 14a.

Therefore, in the hood main body 10a of this embodiment, a circumferential wall part is notched at a position of the visual field angle A2 in a direction corresponding to the length L2 in the diagonal direction of the observation image 14a at the end portion of the protruding portion 11. As a result, the first concave portion 12 is formed at a part in the circumferential direction (diagonal direction of the observation image 14a) of the hood main body 10a in order to avoid the so-called visual field vignetting that the visual field of the endoscope is cut off by the end portion of the protruding portion 11.

Furthermore, the second concave portion 14 of the protruding portion 11 of the hood main body 10a is set as follows. Here, so-called vignetting of the illumination light which is a phenomenon where the shadow 13 of the protruding portion 11 of the endoscopic hood 10 is inserted into the observation image of the endoscope is apt to occur in the following positional relationship. That is, it tends to occur in a range that the positional relationship between a hood wall of the hood main body 10a, the object lens 9 and the illumination lens 7 is that a distance between the hood wall surface and the illumination lens 7 is shorter than a distance between the hood wall surface and the object lens 9 as shown in FIG. 3. This positional relationship corresponds to a range of θ1 along the circumferential direction of the cylinder of the hood main body 10a in FIG. 2.

Therefore, at the end portion of the protruding portion 11 of the hood main body 10a according to this embodiment, the second concave portion 14 used to eliminate the shadow is formed by notching the end portion of the protruding portion 11 at a part of the range θ1 of this positional relationship as shown in FIG. 3. Moreover, the shadow 13 of the protruding portion 11 is eliminated by irradiating the part of the shadow 13 of the protruding portion 11 of the hood main body 10a inserted into the visual field angle of the object lens 9 with the illumination light passing through this second concave portion 14.

Thus, the above-described structure demonstrates the following advantages. That is, in the endoscopic hood 10 according to this embodiment, the second concave portion 14 used to eliminate the shadow is provided at the end portion of the protruding portion 11. As a result, this avoids the so-called vignetting of the illumination light that the shadow 13 of the protruding portion 11 of the hood main body 10a is inserted into the observation image of the object lens 9 of the endoscope. Therefore, when emitting the illumination light from the illumination lens 7 of the endoscope, the part of the shadow 13 of the protruding portion 11 of the hood main body 10a inserted into the visual field angle of the object lens 9 can be irradiated with the illumination light passing through this second concave portion 14. As a result, the shadow 13 of the protruding portion 11 can be eliminated. Consequently, it is possible to provide the endoscopic hood 10 with excellent observation performance which can reduce the shadow 13 in the observation screen of the endoscope caused due to vignetting of the illumination light without degrading the function of the hood main body 10a.

It is to be noted that the first concave portion 12 and the second concave portion 14 may be placed at the same position in the front view of FIG. 2 in some cases. In the side view of FIG. 3, if the concave portion is formed deeper than a minimum depth required to carry out the function as the first concave portion 12 and it serves as the second concave portion 14, this structure is included in the scope of the present invention.

Figure 5:
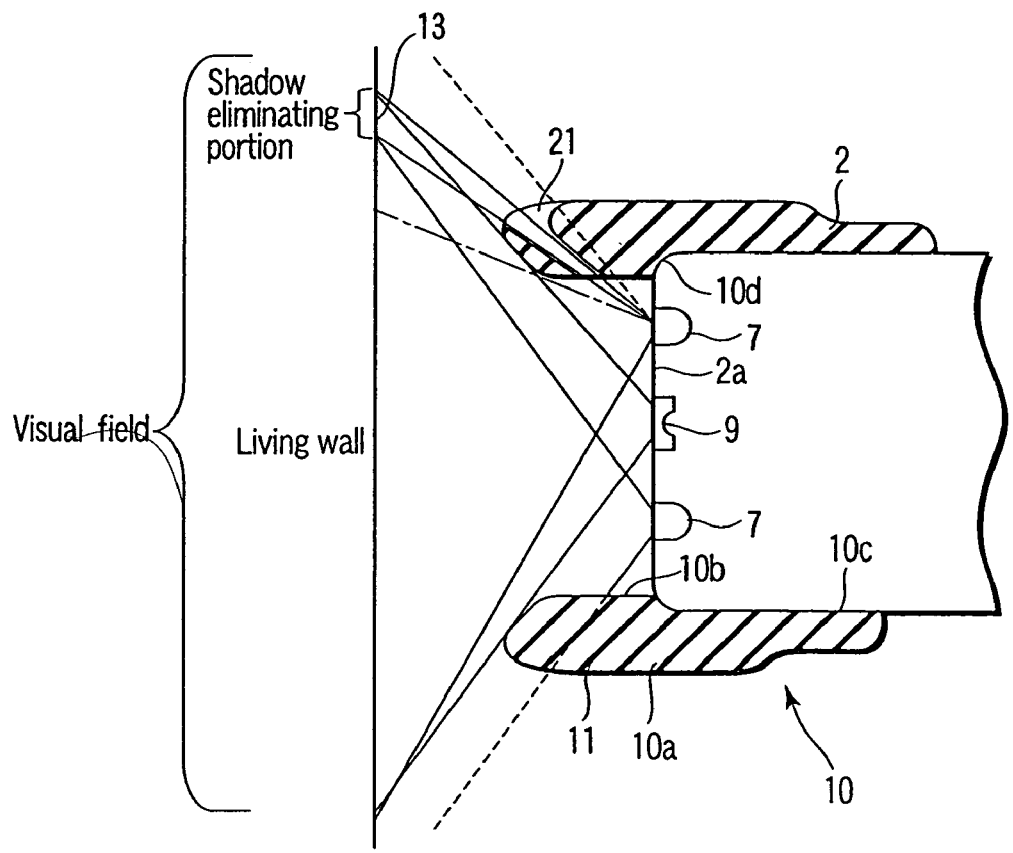
FIG. 5 is a vertical cross-sectional view of a primary part of an endoscopic hood showing a second embodiment according to the present invention.

Additionally, FIG. 5 shows a second embodiment according to the present invention. In this embodiment, the structure of the endoscopic hood 10 according to the first embodiment (see FIGS. 1 to 4) is changed as follows.

That is, in the endoscopic hood 10 according to this embodiment, a hole 21 used to lead the light is formed on a wall surface of the protruding portion 11 in place of the second concave portion 14 used to eliminate the shadow according to the first embodiment. Further, the shadow 13 of the protruding portion 11 is eliminated by irradiating the part of the shadow 13 of the protruding portion 11 of the hood main body 10a inserted into the visual field angle of the object lens 9 with the illumination light from the illumination lens 7 led through this hole 21 on the wall surface of the protruding portion 11.

Furthermore, in the endoscope according to this embodiment, one object lens 9 of the observation optical system and two illumination lenses 7 of the illumination optical system are provided on the end surface 2a of the end portion 2. Moreover, in this embodiment, the hole 21 is formed on the wall surface of the protruding portion 11 in a range that a positional relationship between the hood wall of the hood main body 10a, the object lens 9 and one illumination lens 7 is that a distance between the hood wall surface and the illumination lens 7 is shorter than a distance between the hood wall surface and the object lens 9 like the first embodiment. Additionally, the shadow 13 of the protruding portion 11 is eliminated by the illumination light passing through this hole 21 on the wall surface of the protruding portion 11, thereby avoiding vignetting of the illumination light.

Thus, in the endoscopic hood 10 according to this embodiment, the hole 21 used to eliminate the shadow is provided at the end portion of the protruding portion 11. Further, when emitting the illumination light from the illumination lenses 7 of the endoscope, the part of the shadow 13 of the protruding portion 11 of the hood main body 10a is irradiated with the illumination light passing through this hole 21. As a result, the shadow 13 of the protruding portion 11 inserted into the visual field angle of the object lens 9 can be eliminated. Therefore, it is possible to avoid the so-called vignetting of the illumination light where the shadow 13 of the protruding portion 11 of the hood main body 10a is inserted into the observation image of the object lens 9 of the endoscope. Therefore, it is possible to provide the endoscopic hood 10 with the excellent observation performance which can reduce the shadow 13 in the observation screen of the endoscope caused due to vignetting of the illumination light without degrading the function of the hood main body 10a like the first embodiment.

Furthermore, in this embodiment, since the hole 21 used to eliminate the shadow is provided at the end portion of the protruding portion 11, the end portion of the protruding portion 11 can be extended to the end position over the entire circumferential direction. Therefore, the strength of the endoscopic hood 10 can be substantially evenly assured over the entire circumferential direction of the protruding portion 11. As a result, the degradation of the function of the hood main body 10a can be further reduced.

It is to be noted that the structure that the hole 21 used to lead the light is provided on the wall surface of the protruding portion in accordance with one of the two illumination lenses 7 is illustrated in connection with this embodiment, but it is possible to adopt a structure that respective holes 21 used to lead the light are formed on the wall surface of the protruding portion 11 in accordance with the two illumination lenses 7.

Figure 6:
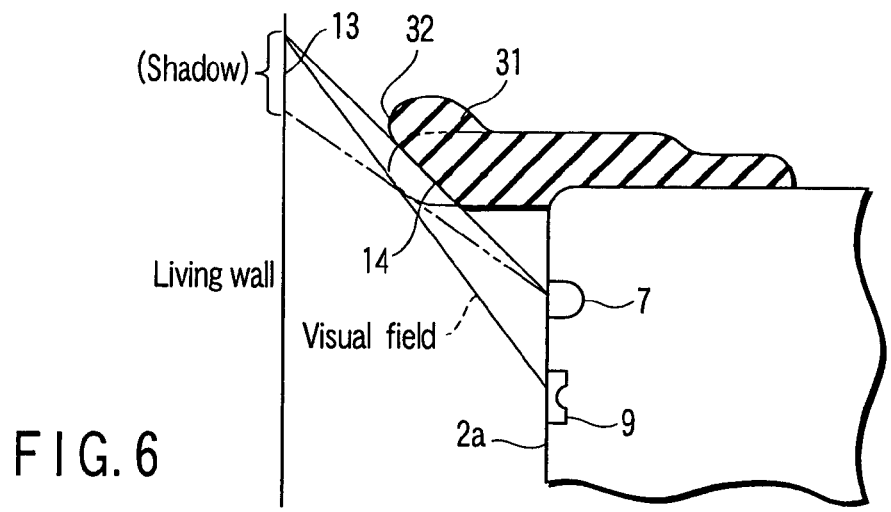
FIG. 6 is a vertical cross-sectional view of a primary part of an endoscopic hood showing a third embodiment according to the present invention.
Figure 7A:
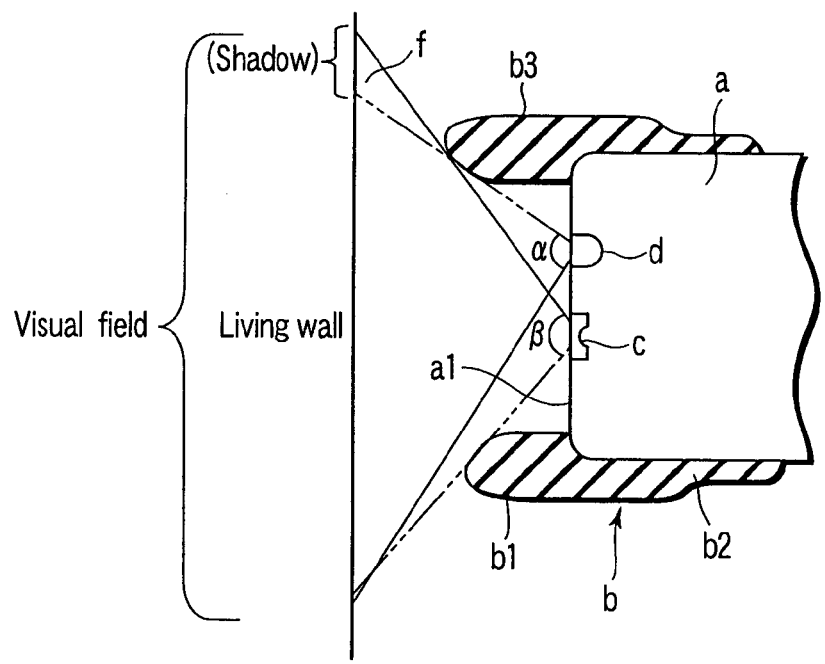
FIG. 7A is an explanatory view for illustrating a state that a shadow of a hood main body is formed in an observation visual field range of the endoscope.
Figure 7B:
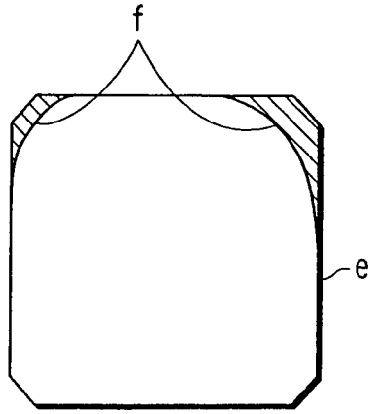
FIG. 7B is a front view showing a shadow of a protruding portion displayed on a monitor of an endoscopic apparatus.

Moreover, FIG. 6 shows a third embodiment according to the present invention. In this embodiment, the structure of the endoscopic hood 10 according to the first embodiment (see FIGS. 1 to 4) is changed as follows.

That is, in the endoscopic hood 10 according to this embodiment, a bending portion 31 which is obliquely bent toward the outside is provided at the end portion of the protruding portion 11 in place of the second concave portion 14 used to eliminate the shadow according to the first embodiment. Additionally, an inclined surface 32 for leading the light which is inclined at substantially the same angle as an outgoing radiation angle of the illumination light from the illumination lens 7 is formed on an inner peripheral surface of an end portion of the bending portion 31.

Thus, in the endoscopic hood 10 according to this embodiment, when emitting the illumination light from the illumination lens 7 of the endoscope, the part of the shadow 13 of the protruding portion 11 of the hood main body 10a can be irradiated with the illumination light passing through the inclined surface 32 for leading the light in the bending portion 31 of the protruding portion 11. Therefore, the shadow 13 of the protruding portion 11 inserted into the visual field angle of the object lens 9 can be eliminated. As a result, it is possible to provide the endoscopic hood 10 with excellent observation performance which can reduce the shadow 13 in the observation screen of the endoscope caused due to vignetting of the illumination light without degrading the function of the hood main body 10*a* as in the first embodiment.

Further, in this embodiment, the bending portion 31 which is obliquely bent toward the outside is provided at the end portion of the protruding portion 11, and the inclined surface 32 for leading the light is provided on the inner peripheral surface of the end portion of this bending portion 31. Therefore, the end portion of the protruding portion 11 can be extended to the end position over the entire circumferential direction. As a result, in this embodiment, the strength of the endoscopic hood 10 can be substantially evenly assured over the entire circumferential direction of the protruding portion 11 as in the second embodiment, thereby further suppressing the degradation of the function of the hood main body 10*a*.

Furthermore, the present invention is not restricted to the foregoing embodiments, and various modifications can be of course carried out without departing from the scope of the present invention.

As described above, the present invention is effective in the technical field where the endoscopic hood is used being attached at the end portion of the elongated insertion portion of the endoscope which is inserted into a lumen, and the technical field where this endoscopic hood is manufactured and used.

What is claimed is:

1. An endoscopic hood comprising:
   a cylindrical hood main body having an attachment portion fitted on an outer peripheral surface of an end portion of an insertion portion of an endoscope, and a protruding portion protruding from an end surface of the insertion portion of the endoscope in an axial direction of the insertion portion; and
   an illumination light leading portion provided on a part of the protruding portion positioned to block irradiation of illumination light to an observation visual field range of the endoscope, the illumination light leading portion being provided to pass illumination light to at least one part of the observation visual field range in which irradiation of the illumination light is blocked by the part of the protruding portion,
   wherein the illumination light leading portion has at least one hole formed on a circumferential wall surface of the part of the protruding portion.

2. The endoscopic hood of claim 1, comprising:
   a second illumination light leading portion provided on the protruding portion, the second illuminating light portion configured to pass the illumination light rays with which a part of the observation visual field range of an object lens of the endoscope is illuminated, the second illumination light leading portion being arranged at such a position that a distance from an illumination lens emitting the illumination light rays of the endoscope is shorter than a distance from the object lens,
   wherein the second illumination light leading portion has at least one hole formed on a circumferential wall surface of the protruding portion.

3. The endoscopic hood according to claim 2, wherein the hood main body is non-removably attached to the outer peripheral surface of the end portion.

4. The endoscopic hood according to claim 2, wherein the illumination light leading portion has a concave portion formed by notching an end portion of the protruding portion.

5. The endoscopic hood according to claim 4, wherein the protruding portion is molded at substantially the same angle as an outgoing radiation angle of the illumination light rays outgoing from the illumination lens.

6. The endoscopic hood according to claim 2, wherein the protruding portion is set at substantially the same angle as an outgoing radiation angle of the illumination light rays outgoing from the illumination lens.

7. The endoscopic hood according to claim 2, wherein the protruding portion has an end portion molded into a shape such that the end portion is absent from the observation visual field.

8. The hood of claim 2, wherein the hood main body is removably attached to the outer peripheral surface of the end portion.

9. The endoscopic hood according to claim 1, wherein the illumination light leading portion has a concave portion on the part of the protruding portion, the concave portion being formed by notching the end portion of an protruding portion.

10. The endoscopic hood according to claim 1, wherein the protruding portion is substantially cylindrical.

11. The endoscopic hood according the claim 10, wherein the substantially cylindrical protruding portion is formed continuously in a circumferential direction thereof.

12. The endoscopic hood according to claim 10, wherein the protruding portion is formed to have substantially the same inside diameter at an end portion and a base end portion.

13. The endoscopic hood according to claim 10, wherein the illumination light leading portion includes:
    a bending portion formed on an end of the protruding portion so that the inner periphery surface of the protruding portion is bent outwardly from a center toward a diameter direction; and
    a sloping surface set at substantially the same angle as the outgoing radiation angle of the illumination light outgoing from the illumination lens.

14. The endoscopic hood according to claim 1, wherein the protruding portion is formed continuously and substantially along an outer peripheral surface of the end portion of the insertion portion of the endoscope.

* * * * *